United States Patent [19]

Naylor et al.

[11] Patent Number: 4,908,370

[45] Date of Patent: Mar. 13, 1990

[54] ANXIOLYTIC-N-(1-AZABICYCLO(2.2.2)OCT-3-YL) BENZAMIDES AND THIOBENZAMIDES

[75] Inventors: Robert J. Naylor; Brenda Naylor, both of Ilkley, England

[73] Assignee: A. H. Robbins Company, Inc., Richmond, Va.

[21] Appl. No.: 133,410

[22] Filed: Dec. 15, 1987

[30] Foreign Application Priority Data

Dec. 16, 1986 [GB] United Kingdom ............ 8629962
Apr. 22, 1987 [GB] United Kingdom ............ 8709508
Jul. 20, 1987 [GB] United Kingdom ............ 8717050

[51] Int. Cl.$^4$ ............................................. A61U 31/44
[52] U.S. Cl. ........................................................ 514/305
[58] Field of Search ........................................... 514/305

[56] References Cited

U.S. PATENT DOCUMENTS 4,093,734  6/1978  Kruger, et al. .................. 544/165
4,593,034  6/1986  Munson, Jr. et al. ............ 514/305

FOREIGN PATENT DOCUMENTS 0099789  2/1984  European Pat. Off. .
0158532  10/1985 European Pat. Off. .
021165   11/1986 European Pat. Off. .
0202062  11/1986 European Pat. Off. .
2125398  3/1984  United Kingdom .

OTHER PUBLICATIONS

Mikhlina, E. E. et al., *Chemical Abstracts,* 69:2220 (b), (1966).
Krueger, G., et al., *Chemical Abstracts,* 87:68001 (c), (1977).
Mikhlina, E. E., et al., *Chemical Abstracts,* 79:146358 (a), (1973).

*Primary Examiner*—Stanley J. Friedman
*Attorney, Agent, or Firm*—Saidman, Sterne, Kessler & Goldstein

[57] ABSTRACT

Compounds of general formula I:

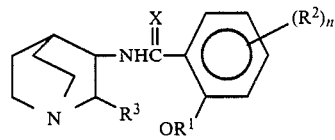

wherein:
  X represents oxygen or sulphur;
  $R^1$ represents loweralkyl;
  $R^2$ represents hydrogen, halo, 4,5-benzo, loweralkoxy, amino, methylamino or dimethylamino;
  $R^3$ represents hydrogen or loweralkyl; and
  n is 1 or 2 and their pharmaceutically acceptable acid addition salts have anxiolytic activity. In particular, they have activity against anxiety induced by the withdrawal from ingested substances such as narcotics (e.g. cocaine), alcohol and nicotine.

16 Claims, 1 Drawing Sheet

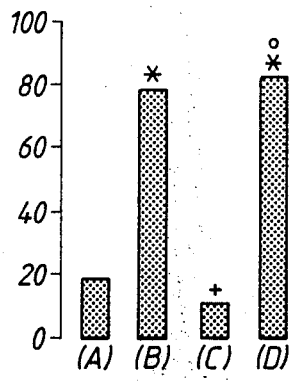
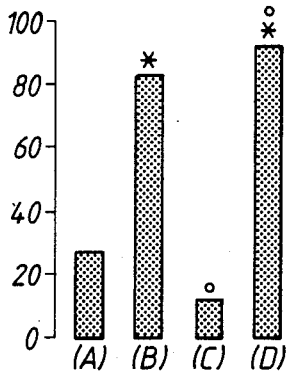
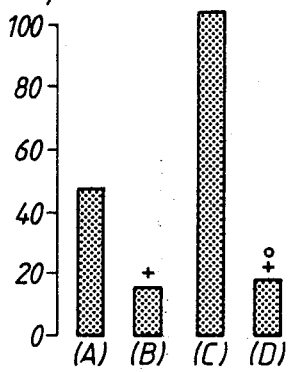
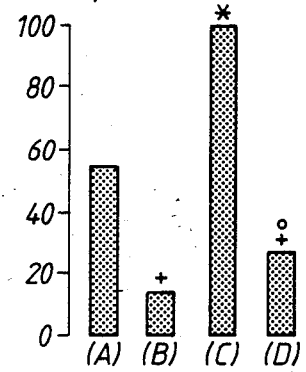

ANXIOLYTIC-N-(1-AZABICYCLO(2.2.2)OCT-3-YL) BENZAMIDES AND THIOBENZAMIDES

The present invention relates to the use of certain N-(3-quinuclidinyl)benzamides and thiobenzamides, namely N-(3-quinuclidinyl)-benzamides and thiobenzamides, otherwise known as N-(1-azabicyclo[2.2.2]oct-3-yl)benzamides and thiobenzamides, which have been observed to exhibit anxiolytic (antianxiety) properties in warm blooded animals. Not only have compounds useful in the present invention been found to have general anxiolytic activity, but also they have been found to be useful in the treatment of anxiety caused by withdrawal from ingested substances such as alcohol, narcotics (such as cocaine) and nicotine.

Quinuclidine analogues of sulpiride were prepared and studied by Mikhlina, E. E. et al as reported in *Khim-Farmatsevt. Zh.* 10, No. 11, 56–60 (1976); C.A. 85: 155489r exemplified by the compound: 5-aminosulphonyl-N-(1-azabicyclo[2.2.2]oct-3-yl)-2-methoxybenzamide. The above named compound was reported in USSR Pat. No. SU-A-414261 to have neuroleptic activity.

Syntheses of 4-amino-N-(1-azabicyclo[2.2.2]oct-3-yl)benzamide and N-(1-azabicyclo[2.2.2]oct-3-yl)benzamide were reported by Mikhlina, E. E. et al in *Khim-Farmatsevt. Zh.* 7, 20–24 (1974); C.A. 79, 146458a and the latter in *Khim.Geterosikl. Soedin., Akad. Nauk. Latv. SSR* 243–9 (1966); C.A. 65: 2220b. These compounds were reported to exhibit hypotensive, narcotic and ganglionic stimulation and blocking activities. Synthesis of 4-amino-N-(1-azabicyclo[2.2.2]oct-3-yl)-3-chloro-5-trifluoromethylbenzamide was reported in DE-A-No. 2548968; C.A. 87, 68001c and in equivalently related U.S. Pat. No. 4,093,734 from 4-amino-3-chloro-5-trifluoromethyl benzoic acid chloride and 3-aminoquinuclidine. The compound is in a class among pyrrolidinyl and piperidinyl benzamides which are said to be useful as anxiolytics, anticonvulsives, antiemetics and antiulcerogenics. None of the compounds have orthoalkoxy substitution on benzamide as do the compounds useful in the present invention.

It is widely recognized that substituted benzamides are a class of drugs known to be effective in psychiatry and gastroenterology (Sulpiride and other Benzamides; International Workshop on Sulpiride and other benzamides, Florence, Feb. 17–18 (1978), Raven Press]. EP-A-No. 0099789 and FR-A-No. 2529548 disclose certain N-(1-azabicyclo[2.2.2]oct-3-yl) benzamides and their use as gastrointestinal motility accelerators.

U.S. Pat. No. 4,593,034 and EP-A-No. 0158532 disclose the treatment of emesis caused by the administration of platinum anticancer drugs (such as cisplatin) by the use of 2-alkoxy-N-(1-azabicyclo[2.2.2]oct-3-yl) benzamides or thiobenzamides.

EP-A-No. 0201165 generically describes a large class of compounds, covering certain N-(1-azabicyclo[2.2.2]oct-3-yl) benzamides and reports that they are useful in the treatment of emesis, anxiety and/or irritable bowel syndrome (IBS). It has now unexpectedly been discovered that various N-(1-azabicyclo[2.2.2]oct-3-yl)benzamides exhibit anxiolytic activity in warm blooded animals. Not only have compounds useful in the present invention been found to have general anxiolytic activity, but also they have been found to be useful in the treatment of anxiety caused by withdrawal from ingested substances such as alcohol, narcotics (for example cocaine) and nicotine.

According to a first aspect of the present invention, there is provided the use of a compound of general formula I:

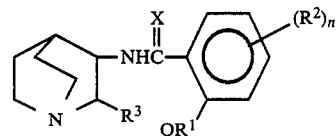

wherein:
X represents oxygen or sulphur;
$R^1$ represents loweralkyl;
$R^2$ represents hydrogen, halo, 4,5-benzo, loweralkoxy, amino, methylamino or dimethylamino;
$R^3$ represents hydrogen or loweralkyl; and
n is 1 or 2 or a pharmaceutically acceptable acid addition salt thereof, in the manufacture of a medicament having anxiolytic activity.

$R^2$ may represent a 3- or 5-halo substituent; it is preferred that alternatively or additionally $R^2$ represent a 4-amino, 4-methylamino or 4-dimethylamino. X may represent oxygen. Preferred $R_3$ substituents are $C_{1-4}$ alkyl, eg methyl or ethyl. The stereochemistry of the substituents on the quinuclidine ring is preferably trans, e.g.:

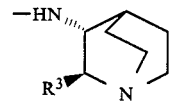

It can be seen that the invention encompasses the use of:
4-amino-N-(1-azabicyclo[2.2.2]oct-3-yl)-5-chloro-2-methoxybenzamide,
N-(1-azabicyclo[2.2.2]oct-3-yl)-5-chloro-2-methoxy-4-methylaminobenzamide,
N-(1-azabicyclo[2.2.2]oct-3-yl)-2-methoxybenzamide,
N-(1-azabicyclo[2.2.2]oct-3-yl)-2,4-dimethoxybenzamide,
N-(1-azabicyclo[2.2.2]oct-3-yl)-2-propoxybenzamide,
4-amino-N--(1-azabicyclo[2.2.2]oct-3-yl)-5-chloro-2-methoxybenzamide,
N-(1-azabicyclo[2.2.2]oct-3-yl)-5-chloro-2-methoxy-4-methylaminobenzamide,
N-(1-azabicyclo[2.2.2]oct-3-yl)-3-methoxy-2-naphthalenecarboximide,
4-amino-N-(1-aza-2-methyl-bicyclo[2.2.2]oct-3-yl)-5-chloro-2-methoxybenzamide, or a pharmaceutically acceptable salt thereof, in the manufacture of a medicament having anxiolytic activity.

The use of 4-amino-N-(1-azabicyclo[2.2.2]oct-3-yl)-5-chloro-2-methoxybenzamide whether as the free base or a salt (for example fumarate or hydrochloride) forms a particularly preferred aspect of the invention.

Insofar as the law allows, the invention encompasses a method for the treatment or prophylaxis of anxiety, and in particular anxiety induced by withdrawal from ingested substances such as alcohol, narcotics (e.g. cocaine) and nicotine, comprising the administration of an anxiolytically effective amount of a compound as described above.

EP-A-No. 0158532 dicloses that certain of the above compounds have gastrokinetic and anti-emetic activity at relatively high daily doses of from 5 to 300 mg. Unit doses of from 0.05 mg to 100 mg are suggested, with from 5 mg to 50 mg or 100 mg active ingredient per unit dose being preferred. According to a second aspect of the present invention, there is provided a pharmaceutical composition comprising a compound of general formula I as defined above, or a pharmaceutically acceptable acid addition salt thereof, and a pharmaceutically acceptable carrier therefor, the composition being adapted to deliver less than 5 mg of the compound of general formula I per day. According to a third aspect of the invention, there is provided a pharmaceutical composition in unit dose form, the composition comprising up to 50 mcg or even 500 mcg of a compound of general formula I and a pharmaceutically acceptable carrier therefor. Preferred features of the second and third aspects of the invention are as for the first aspect, *mutatis mutandis*.

Compounds of general formula I wherein $R^3$ does not represent hydrogen are not disclosed in EP-A-No. 0158532 or FR-A-No. 2529548. According to a fourth aspect of the invention, there is therefore provided a pharmaceutical composition comprising a compound of general formula IA:

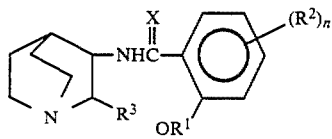

wherein:
X represents oxygen or sulphur;
$R^1$ represents loweralkyl;
$R^2$ represents hydrogen, halo, 4,5-benzo, loweralkoxy, amino, methylamino or dimethylamino;
$R^3$ represents loweralkyl; and
n is 1 or 2, or a pharmaceutically acceptable acid addition salt thereof, and a pharmaceutically acceptable carrier therefor.

$R^2$ may represent a 5-halo substituent; it is preferred that alternatively or additionally $R^2$ represent a 4-amino, 4-methylamino or 4-dimethylamino. X may represent oxygen. Preferred $R_3$ substituents are $C_{1-4}$ alkyl, eg methyl or ethyl. The stereochemistry of the substituents on the quinuclidine ring is preferably trans, e.g.:

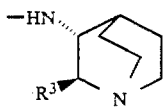

4-Amino-N-(1-aza-2-methyl-bicyclo[2.2.2]oct-3-yl)-5-chloro-2-methoxybenzamide and its pharmaceutically acceptable salts (for example the hydrochloride and fumarate salts) are preferred features of this aspect of the invention.

In the further definition of symbols in the formulae hereof and where they appear elsewhere throughout this specification and the claims, terms have the following significance.

The term "$C_1$-$C_8$alkyl" as used herein includes straight and branched chain radicals of up to eight carbons inclusive and is exemplified by such groups as methyl, ethyl, propyl, isopropyl, butyl, amyl, hexyl, heptyl, and octyl radicals and the like. The term "$C_1$-$C_8$alkoxyl" has the formula —O—$C_1$-$C_8$alkyl. The terms "$C_1$-$C_4$alkyl" and "$C_1$-$C_4$alkoxyl" refer to preferred subclasses of radicals and are to be construed as containing up to four carbon atoms accordingly.

The terms "halo" or "halogen" when referred to herein include fluorine, chlorine, bromine and iodine unless otherwise stated. Chlorine and bromine are preferred. "Pharmaceutically acceptable salts" include the acid addition salts, hydrates, alcoholates and salts of the compounds, which salts are physiologically compatible in warm blooded animals. The acid addition salts may be formed by either strong or weak acids. Representative of strong acids are hydrochloric, sulphuric and phosphoric acids. Representative of weak acids are fumaric, maleic, succinic, oxalic, citric, tartaric, cyclohexamic and the like.

The term "pharmaceutical" is to be understood as including "veterinary" where the context so admits, and cognate terms should be construed accordingly.

Protected amino groups used in synthesis are acetylamino or benzoylamino radicals and the like on the benzamide moiety mentioned hereinbelow in synthetic methods.

The anxiolytic activity was determined by a method of Costall et al, details of which are to be found in the pharmacology examples later in this specification. In brief, the method involves seeing whether the compound under test reduced the natural anxiety of mice in brightly-lit areas.

PREPARATION OF BENZAMIDES

Benzamido compounds of Formula I are preparable by reacting a suitably activated benzoic acid derivative with 3-aminoquinuclidine to form the corresponding benzamide under a variety of conditions. Two general methods, A and B, are illustrated in the following equations:

Method A, using an Acid Chloride

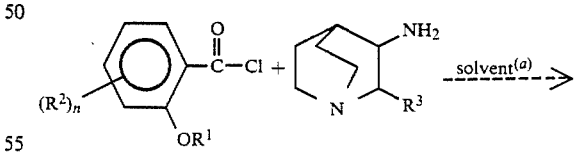

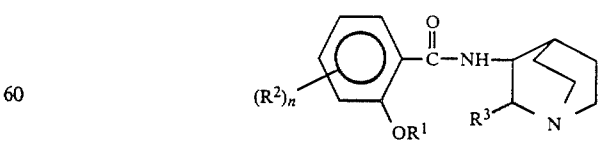

$R^1$, $R^2$, $R^3$ and n are as defined under general formula I except that $R^2$ cannot be unprotected amino.

(a) Suitable solvents are chloroform and diethyl ether.

Method A is illustrated by Examples 5, 6, 7 and 9.

Method B, using 1,1'-carbonyldiimidazole

[Reaction scheme: Ar(R²)ₙ(OR¹)-COOH + carbonyldiimidazole + 3-aminoquinuclidine (NH₂, R³) → benzamide product, (1) solvent(a), (2); (a) e.g., tetrahydrofuran]

R¹, R², R³ and n are as defined under general formula I (a) e.g., tetrahydrofuran Method B is illustrated in Examples 1, 3 and 8.

Compounds wherein R₂ is primary amino may also be prepared from a compound prepared by Methods A or B, wherein R₂ is nitro by catalytic reduction of the nitro compound.

Alternatively, compounds wherein R₂ is amino may be prepared by procedures of Method A utilizing a starting benzoyl halide wherein the amino group has been protected, or they may be prepared from compounds prepared in Method A or B wherein R₂ is nitro and reducing the nitro radical to an amino radical.

Preferably, the compounds wherein R₂ is amino or methylamino are prepared by Method B.

The free base of any compound of Formula I from its acid addition salt may be regenerated by usual procedures of partitioning between dilute aqueous base and a suitable solvent, separating the solvent layer, drying and evaporating.

PREPARATION OF THIOBENZAMIDES

The preparation of the thiobenzamido compounds of Formula I' may be accomplished by mixing and reacting a benzamido compound of Formula I with a mixture of phosphorus pentasulphide (P₂S₅) and potassium sulphide (K₂S) or by mixing and reacting 3-aminoquinuclidine with an appropriately substituted benzaldehyde and sulphur. The reaction sequences are illustrated by the following:

[Reaction scheme showing benzamide + P₂S₅/K₂S → thiobenzamide; and 3-aminoquinuclidine + benzaldehyde + S → thiobenzamide]

In these methods, compounds wherein R₂ is nitro may be reduced to compounds wherein R₂ is amino.

A preferred group of compounds encompassed by Formula I have the formula:

[Structure of 4-amino-5-chloro-2-methoxy-N-(quinuclidin-3-yl)benzamide with Am substituent]

wherein Am is amino (i.e., —NH₂) or methylamino. As will be recognized from the above description, these compounds (Ic) are preferably prepared by Method B.

It is therefore a primary object to provide N-(1-azabicyclo[2.2.2]oct-3-yl)benzamides and thiobenzamides.

A further object is to provide N-(1-azabicyclo[2.2.2]oct-3-yl)benzamides and thiobenzamides having antianxiety properties.

A still further object is to provide means for controlling anxiety.

The invention will now be illustrated by the following non-limiting examples.

EXAMPLE 1

4-Amino-N-(1-azabicyclo[2.2.2]oct-3-yl)-5-chloro-2-methoxybenzamide, fumarate [1:1].
(4-Amino-5-chloro-2-methoxy-N-(quinuclidin-3-yl)benzamide, fumarate [1:1]).

In a closed system equipped with an oil bubbler, 30 ml of tetrahydrofuran was added to a mixture of 4-amino-5-chloro-2-methoxybenzoic acid, 2.02 g, (0.010 mole) and 1,1'-carbonyldiimidazole, 1.62 g (0.010 mole) with stirring. When evolution of carbon dioxide ceased, nitrogen was bubbled through the reaction mixture for 1 hr. A solution of 3-aminoquinuclidine, 1.26 g, (0.010 mole) in 10 ml tetrahydrofuran was added dropwise to the stirred reaction mixture and stirring at room temperature continued for 3 hrs. TLC analysis (3% conc. ammonium hydroxide solution in methanol) showed some product formation. The mixture was heated at reflux temperature for 18 hours and then concentrated to an oil. TLC analysis showed the prsence of the product, imidazole, and 3-aminoquinuclidine. The oil was dissolved in methylene chloride (75 ml) and washed twice with 50 ml protions of aqueous sodium bicarbonate solution. The methylene chloride layer was dried over anhydrous magnesium sulphate and concentrated to yield 2.0 g (67%) of a glassy amorphous solid, the free base of the title compound.

In another reaction on a 0.020 mole scale, 5.18 g (83.8%) of the product as the free base was obtained.

The products were combined, dissolved in methanol (20 ml) and the solution and treated with a solution of fumaric acid (2.73 g) in methanol (50 ml). Absolute ether was added to precipitate the salt which was collected by filtration and recrystallized from methanol-water (200:20) with isopropyl ether added to the point of incipient cloudiness. The recrystallized salt (5.38 g) melted at 223°–225° C.

Analysis: Calculated for $C_{19}H_{24}N_3O_6Cl$: C,53.59; H,5.68;
N,9.89
Found : C,53.35; H,5.72;
N,9.95.

EXAMPLE 2

4-Amino-N-(1-azabicyclo[2.2.2]oct-3-yl)-5-chloro-2-methoxybenzamide, hydrochloride, hydrate (1:1:1). (4-Amino)-5-chloro-2-methoxy-N-(quinuclidin-3-ylbenzamide, hydrochloride, hydrate (1:1:1)).

To an isopropyl alcohol solution of the free base of the title compound such as was obtained by the procedure of Example 1 is added an equal molar amount of 37% (conc.) hydrochloric acid. The crude salt is separated by filtration and recrystallized from acetone-water to give the title compound, m.p. 158°–160° C.

EXAMPLE 3

N-(1-Azabicyclo[2.2.2]oct-3-yl)-5-chloro-2-methoxy-4-(methylamino)benzamide, fumarate [1:1]. (5-chloro-2-methoxy-4-methylamino-N-(quinuclidin-3-yl)benzamide, fumarate [1:1]).

To a mixture of 1,1'-carbonyldiimidazole, 1.23 g (0.00756 mole) and 5-chloro-2-methoxy-4-methylaminobenzoic acid, 1.63 g (0.00756 mole) was added 50 ml of tetrahydrofuran. Nitrogen was bubbled into the solution for 30 minutes to remove any carbon dioxide that was present. To the solution was added 3-aminoquinuclidine, 0.95 g, (0.00756 mole) in one portion, and the reaction mixture was stirred at ambient temperature for 16 hours. The reaction mixture was concentrated to an oil which was shown to be 1:1 mixture of the free base of the product and imidazole. The mixture was dissolved in 20 ml methanol and treated with a solution containing 0.47 g fumaric acid in 20 ml of hot methanol. Upon cooling, 1.52 g of white solid formed. Recrystallization from water-methanol gave 0.84 g of the product as a white solid; m.p. 237°–238° C.

Analysis: Calculated for $C_{20}H_{26}N_3O_6Cl$: C,54.61; H,5.96;
N,9.55
Found : C,54.61; H,5.98;
N,9.51.

EXAMPLE 4

N-(1-Azabicyclo[2.2.2]oct-3-yl)-5-chloro-2-methoxy-4-(methylamino)-benzamide, hydrochloride (1:1). (5-chloro-2-methoxy-4-(methylamino)-N-(quinuclidin-3-yl)benzamide, hydrochloride (1:1).

To an isopropyl alcohol solution of the free base of the title compound, such as was obtained by the procedure of Example 3, is added an equal molar amount of 37% (conc.) hydrochloric acid. The crude salt is separated by filtration and recrystallized from ethanol-water to give the title compound, m.p. 255°–258° C.

EXAMPLE 5

N-(1-Azabicyclo[2.2.2]oct-3-yl)-2-methoxybenzamide, fumarate [1:1]hemihydrate. (2-methoxy-N-(quinuclidin-3-yl)benzamide, fumarate [1:1]hemihydrate).

In a closed system equipped with an oil bubbler, a solution of 2-methoxybenzoyl chloride, 2.76 g (0.0016 mole) in 50 ml absolute ether was added dropwise over 10 min to a stirred solution of 3-aminoquinuclidine, 1.81 g (0.0144 mole) in 100 ml absolute ether. After the addition was completed, the mixture was stirred at room temperature for an additional 2 hrs. The solid hydrochloride salt was collected by filtration under nitrogen. The salt (3.83 g) was dissolved in sodium bicarbonate solution and extracted twice with 25 ml portions of methylene chloride. The extract was dried over magnesium sulphate and concentrated to yield 1.25 g clear oil (33.3%). TLC analysis (3% conc. ammonium hydroxide in methanol) showed the free base to be pure. A solution of 1.17 g of the free base in 5 ml methanol was treated with a solution of 0.52 g fumaric acid in 10 ml methanol. Isopropyl ether was added to give approximately 100 ml of solution from which the fumarate salt precipitated. The salt was collected under nitrogen and dried in a vacuum oven at 60° C. overnight. NMR and elemental analyses showed that the product was a hemihydrate.

Analysis: Calculated for $C_{19}H_{25}N_2O_{6.5}$: C,59.21; H,6.54;
N,7.27
Found : C,59.18; H,6.30
N,7.25.

EXAMPLE 6

N-(1-Azabicyclo[2.2.2]oct-3-yl)-2,4-dimethoxybenzamide hydrochloride [1:1]. (N-(quinuclidinyl-3-yl)-2,4-dimethoxybenzamide hydrochloride [1:1].

A mixture of 3-aminoquinuclidine dihydrochloride, 6.95 g, (0.0349), 2,4-dimethoxybenzoyl chloride, 700 g, (0.0349 mole), anhydrous sodium carbonate, 36.99 g, (0.349 mile), 175 ml water, and 175 ml chloroform was stirred rapidly to achieve good mixing of the 2 layers for 20 hrs. The chloroform layer was then separated, washed with water, dried over anhydrous magnesium sulphate, and concentrated to an impure oil. The oil was triturated twice with 20 ml portions of petroleum ether to remove some impurities. The oil was then dissolved in ether and filtered to remove a small amount of insoluble material. The filtrate was treated with ethereal hydrogen chloride and the resulting salt collected to yield 2.70 g (23.7% yield) white solid. The salt was recrystallized from ethanol-isopropyl ether. Further recrystallization from methanol-ethyl ether yielded a white solid, m.p. 211°–212° C. The NMR analysis was satisfactory.

Analysis: Calculated for $C_{16}H_{23}N_2O_3Cl$: C,58.80; H,7.09;
N,8.57
Found : C,58.38; H,7.13;
N,8.44

EXAMPLE 7

N-(1-Azabicyclo[2.2.2]oct-3-yl)-2,4-dimethoxybenzamide, sulphate[1:].
(2,4-dimethoxy-N-(quinuclidin-3-yl)benzamide, sulphate[1:]).

In a closed system equipped with an oil bubbler, a solution of 2,4-dimethoxybenzoyl chloride, 13.08 g, (0.0652 mole) in 200 ml absolute ether was added dropwise over 30 minutes to a stirred solution of 3-aminoquinuclidine, 7.80 g, (0.0619 mole) in 200 ml absolute ether. The mixture was stirred overnight, and the solid hydrochloride salt of the product was filtered under nitrogen. The material was dried in a vacuum oven at 40° C. to give 18.70 g (92%). A 2.94 g (0.009 mole) portion of the hydrochloride salt in 20 ml methanol was treated with a solution of sodium methoxide prepared from 0.23 g (0.010 mole) sodium metal and 10 ml methanol. After standing a few minutes, the mixture was filtered and the filtrate concentrated on a rotary evaporator, and the residue was triturated with 75 ml methylene chloride. After filtering to remove some insoluble solids, the filtrate was concentrated to yield 2.53 g of the free base of the title compound (97% recovery from the hydrochloride salt). The free base was dissolved in 100 ml acetone and concentrated sulphuric acid (0.483 ml) added dropwise with stirring. The solid that formed was collected under nitrogen to give 2.76 g of the salt which recrystallized from methanol-isopropyl ether and dried in a vacuum oven at 60 ° C. for 2 hrs and then overnight at 78° C.; m.p. 223°–225° C.

Analysis: Calculated for $C_{16}H_{24}N_2O_7S$: C,49.47; H,6.23;
N,7.23
Found : C,49.41; H,6.30;
N,7.25

EXAMPLE 8

N-(1-Azabicyclo[2.2.2]oct-3-yl)-2,4-dimethoxybenzamide, fumarate [1:1.5].
(2,4-dimethoxy-N-(quinuclidin-3-yl)benzamide, fumarate [1:1.5]).

In a closed system equipped with an oil bubbler, tetrahydrofuran, 100 ml, was added to a mixture of 2,4-dimethoxybenzoic acid, 3.64 g (0.020 mole) and 1,1'-carbonyldiimidazole, 3.24 g (0.020 mole). No evolution of carbon dioxide was observed and after stirring for 3 hrs, TLC (ethyl acetate) and mass spectral analysis showed that the starting material had reacted to form N-(2,4-dimethoxybenzoyl)imidazole and imidazole. A solution of 3-aminoquinuclidine, 2.52 g (0.020 mole) in 10 ml tetrahydrofuran was added to the mixture, and the solution was heated to reflux temperature for 1 hr and then allowed to stand overnight at room temperature. A solution of fumaric acid, 2.32 g (0.020 mole) in 50 ml methanol was added to the reaction mixture. Tetrahydrofuran was added until the solution became slightly turbid. The solution was chilled in a refrigerator. The solid which precipitated from solution was collected by filtration and found to be a fumarate salt of 3-aminoquinuclidine. The filtrate was concentrated to an oil and triturated with tetrahydrofuran. The solid precipitate which formed on standing was filtered and shown by TLC (3% concentrated ammonium hydroxide in methanol) to be the desired product plus traces of imidazole and 3-aminoquinuclidine. Recrystallization from methanolisopropyl ether gave 5.41 g white crystalline solid (67% yield calculated as the monofumarate). NMR and elemental analysis showed the salt to contain less than one equivalent of fumaric acid. The salt was dissolved in boiling methanol (50 ml) and treated with an additional 0.77 g (0.0066 mole) fumaric acid in 10 ml hot methanol. Isopropyl ether was added until the hot solution became turbid. The solid obtained on cooling was collected, recrystallized from methanol-isopropyl ether and dried in a vacuum oven at 78° C. overnight. NMR and elemental analysis showed the salt to be a 1.5 fumarate, m.p. 192°–192.5° C.

Analysis: Calculated for $C_{22}H_{28}N_2O_9$: C,56.89; H,6.08;
N,6.03
Found : C,56.81; H,6.13;
N,6.04

EXAMPLE 9

N-(1-Azabicyclo[2.2.2]oct-3-yl)-2-propoxybenzamide hydrochloride [1:1]. (2-propoxy-N-(quinuclidin-3-yl)benzamide hydrochloride [1:1]).

To a solution of 3.82 g (0.0192 mole) of 3-aminoquinuclidine dihydrochloride in about 25 ml of carbon dioxide-free water was added 8 g (0.025 mole) of barium hydroxide octahydrate. The mixture was warmed for 5 minutes and then dried to a powder on a rotary evaporator. While protecting from contamination with carbon dioxide in the atmosphere, the powder was extracted in sequence with hot benzene and a 1:1 mixture of benzene-methylene chloride solution. The combined extracts were dried over magnesium sulphate and the mixture filtered. To the filtrate with agitation was added dropwise a solution of 3.4 g (0.0171 mole) of 2-propoxybenzoyl chloride in 50 ml of methylene chloride. The mixture was warmed on a steam bath to evaporate about 75% of the methylene chloride. Ligroin (60–110) was added and the mixture solidified. The solid was recrystallized from anhydrous ethyl alcohol to give 3.9 g (62.0%), m.p. 210°–211° C.

Analysis: Calculated for $C_{17}H_{25}N_2O_2Cl$: C,62.86; H,7.75;
N,8.62
Found : C,62.62; H,7.59;
N,8.54

EXAMPLE 10

N-(1-Azabicyclo[2.2.2]oct-3-yl)-3-methoxy-2-naphthalene-carboxamide, hydrochloride [1:1].
(3-methoxy-2-naphthalene-N-(quinuclidin-3-yl)carboxamide, hydrochloride [1:1]).

A solution of 1.69 g (0.00768 mole) of 3-methoxy-2-chloride in 15 ml of methylene chloride was added dropwise to a stirred solution of 0.97 g (0.00768 mole) of 3-aminoquinuclidine in 25 ml of methylene chloride in a closed system equipped with an oil bubbler. The reaction mixture wa stirred overnight at ambient temperature, and then concentrated to give an off-white glassy solid. Two recrystallizations from methanol-isopropyl ether gave 1.95 g (73.4%) of the product as an off-white solid which was vacuum dried at ambient temperature, m.p. 248°–252° C.

Analysis: Calculated for $C_{19}H_{23}N_2O_2Cl$: C,65.79; H,6.68;
N,8.08
Found : C,65.40; H,6.72;
N,8.01.

EXAMPLE 11

4-Amino-N-(1-azabicyclo[2.2.2]oct-3-yl)-5-chloro-2-methoxythiobenzamide fumarate.

(4-Amino-5-chloro-2-methoxy-N-(quinuclidin-3-(yl)thiobenzamide fumarate).

One half mole of 4-amino-N-(1-azabicyclo[2.2.2]oct-3-yl)-5-chloro-2-methoxybenzamide fumarate is partitioned between dilute sodium hydroxide and 400 ml of benzene. The benzene solution is dried with sodium sulphate and distilled to a volume of 250 ml. To this is added a finely-ground mixture of 9 g of phosphorous pentasulphide and 9 g of potassium sulphide. The mixture is refluxed for 4 hr and an additional 9 g of phosphorous pentasulphide is added and reflux continued for 2 hr. The benzene is decanted off. The solid is dissolved in a suitable solvent and reacted with fumaric acid to give the title compound.

EXAMPLE 12

4-Amino-N-(1-aza-2-methylbicyclo[2.2.2]oct-3-yl)-5-chloro-2-methoxybenzamide, fumarate [1:1](4-Amino-5-chloro-2-methoxy-N-(2-methylquinuclidin-3-yl)benzamide, fumarate [1:1])

Following the general procedure of Example 1, but instead of the 3-aminoquinuclidine, using 0.010 moles of 3-amino-2-methylquinuclidine, the title compound was prepared.

EXAMPLE 13

4-Amino-N-(1-aza-2-methylbicyclo[2.2.2]oct-3-yl)-5-chloro-2-methoxybenzamide, hydrochloride, hydrate (1:1:1)
4-Amino-5-chloro-2-methoxy-N-(2-methylquinuclidin-3-yl)benzamide, hydrochloride, hydrate (1:1:1)

To an isopropyl alcohol solution of the free base of the title compound such as was obtained by the procedure of Example 1 is added an equal molar amount of 37% (conc.) hydrochloric acid. The crude salt is separated by filtration and recrystallised from acetone-water to give the title compound.

PHARMACOLOGY EXAMPLE A

Methodology

Experimental Animals

Naive male albino BKW mice, 25-30 g, were used in all experiments. 10 mice were normally housed in each cage and given free access to food and water. The mice were kept on a 12 h light and 12 h dark cycle with lights off at 10:00h and on at 22:00 h.

Anti-anxiety Test

The apparatus used for the detection of changes in anxiety consisted of an open topped box (81×36×27 cm high) one third painted black and illuminated under a dim red light (1×60 W) and partitioned from the remainder of the box which was painted white and brightly illuminated with a 100 W light source located 17 cm above the box. Access between these areas was enabled by means of a 7.5×7.5 cm opening located at floor level in the centre of the partition. The floor area was lined into 9 cm squares. The test was conducted between 13.00 and 18.00 h in a quiet, darkened room illuminated with red light only. Animals were thus taken in a dark container from a dark holding room to the dark testing room.

Animals that had received drug or vehicle injections were placed individually into the centre of the white area and their behaviour observed over a 5 min period by remote video recording. Four behavioural parameters were noted every minute: the number of exploratory rearings in the white and black sections, the number of line crossings in the white and black areas, the number of transitions between the white and black or black and white areas and the time spent in the white and black areas. Experimenters remained blind to drug treatment throughout, with the code only being broken after analysis was complete.

EXPERIMENTAL DESIGN

Animals were used in treatment groups of 7-10 and vehicle controls were run on each day of testing. Results were anlysed using Single-Factor Analysis of Variance followed by Dunnett's procedure for comparing all treatments with control.

DRUG

The compounds of Examples 2 and 4 were administered intraperitoneally in sterile saline in a volume of 1 ml/100 g body weight.

RESULTS

Results are shown in Table 1.

TABLE 1

| Drug (mg/kg) | No of Rearings | |
| --- | --- | --- |
| | White Section | Black Section |
| Control (10 ml/kg) | 16 | 39 |
| Ex 2 0.0001 | 26[a] | 32[a] |
| Ex 2 0.001 | 44[a] | 22[a] |
| Ex 2 0.05 | 39[a] | 22[a] |
| Ex 2 0.1 | 53[a] | 15[a] |
| Ex 2 1 | 54[a] | 15[a] |
| Ex 2 10 | 39[a] | 17[a] |
| Ex 4 1.25 | 68[b] | 17[b] |
| Ex 13 1.25 | 81 | 17 |

| | No of line crossings | |
| --- | --- | --- |
| | White Section | Black Section |
| Control (10 ml/kg) | 46 | 67 |
| Ex 2 0.0001 | 52 | 38[a] |
| Ex 2 0.001 | 58[a] | 13[a] |
| Ex 2 0.05 | 60[a] | 18[a] |
| Ex 2 0.1 | 68[a] | 18[a] |
| Ex 2 1 | 73[a] | 15[a] |
| Ex 2 10 | 71[a] | 18[a] |
| Ex 4 1.25 | 62[b] | 16[b] |
| Ex 13 1.25 | 96 | 20 |

[a] $p < 0.05$ from control
[b] $p < 0.001$ from control

PHARMACOLOGY EXAMPLE B

The procedure of Pharmacology Example A was followed, except that a group of mice (n=5) received 8% ethanol in their drinking water for 14 days; the ethanol treated mice were then withdrawn from the ethanol. Results are shown in Table 2

TABLE 2

| Drug (mg/kg) | No of Rearings | |
| --- | --- | --- |
| | White Section | Black Section |
| Mice without ethanol treatment | | |
| Control (10 ml/kg) | 21 | 33 |
| Ex 2 0.1 | 68[c] | 10[c] |
| Ethanol-treated mice | | |

TABLE 2-continued

| | | |
|---|---|---|
| Control (10 ml/kg) | 10$^c$ | 73$^c$ |
| Ex 2 0.1 | 73$^{cd}$ | 19$^{cd}$ |

| | No of line crossings | |
|---|---|---|
| | White Section | Black Section |
| Mice without ethanol treatment | | |
| Control (10 ml/kg) | 53 | 53 |
| Ex 2 0.1 | 76$^c$ | 23$^c$ |
| Ethanol-treated mice | | |
| Control (10 ml/kg) | 13$^c$ | 100$^c$ |
| Ex 2 0.1 | 80$^{cd}$ | 24$^{cd}$ |

$^c$ p < 0.02 from control
$^d$ p < 0.05 from ethanol-withdrawn mice

PHARMACOLOGY EXAMPLE C

The procedure of Pharmacology Example A was followed, except that a group of mice (n=5) received 1 mg/kg cocaine administered twice daily IP for 14 days; the cocaine-treated mice were then withdrawn from the cocaine. Results are shown in Table 3

TABLE 3

| | No of Rearings | |
|---|---|---|
| Drug (mg/kg) | White Section | Black Section |
| Mice without cocaine treatment | | |
| Control (10 ml/kg) | 22 | 30 |
| Ex 2 0.1 | 50$^e$ | 12$^e$ |
| Cocaine-treated mice | | |
| Control (10 ml/kg) | 15$^e$ | 51$^e$ |
| Ex 2 0.1 | 52$^{ef}$ | 14$^{ef}$ |

| | No of line crossings | |
|---|---|---|
| | White Section | Black Section |
| Mice without cocaine treatment | | |
| Control (10 ml/kg) | 53 | 50 |
| Ex 2 0.1 | 71$^e$ | 15$^e$ |
| Cocaine-treated mice | | |
| Control (10 ml/kg) | 22$^e$ | 82$^e$ |
| Ex 2 0.1 | 75$^{ef}$ | 18$^{ef}$ |

$^e$ p < 0.05 from control
$^f$ p < 0.05 from cocaine-withdrawn mice

PHARMACOLOGY EXAMPLE D

The procedure of Pharmacology Example A was followed, except that a group of mice (n=5) received 0.1 mg/kg nicotine administered twice daily for 7 days; the nicotine-treated mice were then withdrawn from the nicotine. Results are shown graphically in FIG. 1, which illustrates the antagonism of nicotine withdrawal anxiogenesis by the compound of Example 2. In FIG. 1, the columns and symbols have the following significance:
(A)—Control
(B)—Nicotine-treated (but not withdrawn) mice
(C)—Nicotine-withdrawn mice
(D)—Nicotine-withdrawn mice treated with 1.0 mg/kg twice daily Compound of Example 2
*—p<0.001 compared to (A)
+—p<0.001 compared to (A)
o—p<0.001 reversal (C)
The standard errors of the means were less than 12.9%.

PHARMACEUTICAL METHODS AND COMPOSITIONS

Generally, anxiety can be controlled by means of this invention by administering internally to warm blooded animals including human beings certain N-(1-azabicyclo[2.2.2]oct-3-yl)benzamides and thiobenzamides of Formula I, preferably Formula Ic, or a non-toxic organic or inorganic acid addition salt thereof in a wide variety of pharmaceutical forms well known in the art, preferably with a non-toxic pharmaceutical carrier such as is described below in an amount to control anxiety.

The active agent is administering orally, subcutaneously, intravenously or intramuscularly or parenterally and, if necessary, in repeated doses until satisfactory response is obtained. The daily dosage is from about 1 mcg to about 50 mg of active medication, advantageously from about 5 mcg to 5.0 mg. The compositions may contain 5.0 mcg to 50 mg active medicament per unit dose. Preferably, the compositions contain from about 5 mcg to 50 mg of medicament, advantageously from about 5 mcg to about 5.0 mg per unit dose. The compounds may thus be presented in a therapeutic composition suitable for oral, parenteral, subcutaneous, intramuscular, intraperitoneal or intravenous administration. Thus, for example oral administration can take the form of elixirs, capsules, tablets or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone.

For parenteral administration, the carrier or excipient can be comprised of a sterile parenterally acceptable liquid; e.g., water or arachis oil contained in ampoules.

The pharmaceutical compositions may be formulated to contain from about 1.0 mcg/ml to about 50.0 mg/ml, preferably 50 mcg/ml or less. It is only necessary that the active ingredient of Formula I constitute an effective amount.

In all of the above, it is only necessary that a suitable effective dosage will be consistent with the dosage form employed. The exact individual dosages, as well as daily dosages, will of course be determined according to standard medical principles under the direction of a physician or veterinarian.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention, and it is therefore understood that the invention is to be limited only by the scope of the appended claims.

What is claimed is:

1. A method for the treatment or prophylaxis of anxiety comprising the administration to a warm-blooded animal requiring such treatment or prophylaxis of an anxiolytically effective amount of a compound of general formula I:

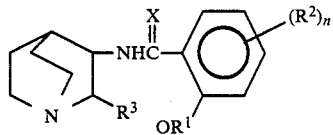

wherein:
X represents oxygen or sulphur;
R$^1$ represents loweralkyl;

R² represents hydrogen, halo, 4,5-benzo, loweralkoxy, amino, methylamino or dimethylamino;
R³ represents hydrogen or loweralkyl; and
n is 1 or 2
or a pharmaceutically acceptable acid addition salt thereof.

2. A method as claimed in claim 1, wherein said anxiety is induced by withdrawal from an ingested substance.

3. A method as claimed in claim 2, wherein said ingested substance is selected from the class consisting of alcohol, narcotics, nicotine and mixtures thereof.

4. A method as claimed in claim 2 wherein said ingested substance is cocaine.

5. A method as claimed in claim 1, wherein, in general formula I, R² represents a 3- or 5- halo substituent.

6. A method as claimed in claim 1 wherein, in general formula I, R² represents a 4-amino, 4-methylamino or 4-dimethylamino substituent.

7. A method as claimed in claim 1, wherein, in general formula I, X represents oxygen.

8. A method as claimed in claim 1, wherein said compound is 4-amino-N-(1-azabicyclo[2.2.2]oct-3-yl)-5-chloro-2-methoxybenzamide, or a pharmaceutically acceptable salt thereof.

9. A method as claimed in claim 1, wherein said compound is N-(1-azabicyclo[2.2.2]oct-3-yl)-5-chloro-2-methoxy-4-methylaminobenzamide, or a pharmaceutically acceptable salt thereof.

10. A method as claimed in claim 1, wherein said compound is N-(1-azabicyclo[2.2.2]oct-3-yl)-2-methoxybenzamide, or a pharmaceutically acceptable salt thereof.

11. A method as claimed in claim 1, wherein said compound is N-(1-azabicyclo[2.2.2]oct-3-yl)-2,4-dimethoxybenzamide, or a pharmaceutically acceptable salt thereof.

12. A method as claimed in claim 1, wherein said compound is N-(1-azabicyclo[2.2.2]oct-3-yl)-2-propoxybenzamide, or a pharmaceutically acceptable salt thereof.

13. A method as claimed in claim 1, wherein said compound is 4-amino-N-(1-azabicyclo[2.2.2]oct-3-yl)-5-chloro-2-methoxybenzamide, or a pharmaceutically acceptable salt thereof.

14. A method as claimed in claim 1, wherein said compound is N-(1-azabicyclo[2.2.2]oct-3-yl)-5-chloro-2-methoxy-4-methylaminobenzamide, or a pharmaceutically acceptable salt thereof.

15. A method as claimed in claim 1, wherein said compound is N-(1-azabicyclo[2.2.2]oct-3-yl)-3-methoxy-2-naphthalenecarboximide, or a pharmaceutically acceptable salt thereof.

16. A method as claimed in claim 1, wherein said compound is 4-amino-N-(1-aza-2-methyl-bicyclo[2.2.2]-oct-3-yl)-5-chloro-2-methoxybenzamide, or a pharmaceutically acceptable salt thereof.

* * * * *